(12) United States Patent
Brown et al.

(10) Patent No.: US 8,617,364 B2
(45) Date of Patent: Dec. 31, 2013

(54) SENSORS AND SENSOR HOUSING SYSTEMS

(75) Inventors: Michael Alvin Brown, Cranberry Township, PA (US); Brian Keith Davis, Butler, PA (US); Towner Bennet Scheffler, Butler, PA (US)

(73) Assignee: Mine Safety Appliances Company, Cranberry Township, PA (US)

( * ) Notice: Subject to any disclaimer, the term of this patent is extended or adjusted under 35 U.S.C. 154(b) by 47 days.

(21) Appl. No.: 13/220,240

(22) Filed: Aug. 29, 2011

(65) Prior Publication Data
US 2013/0048496 A1 Feb. 28, 2013

(51) Int. Cl.
*G01N 27/403* (2006.01)

(52) U.S. Cl.
USPC ............................ 204/400; 204/424; 204/416

(58) Field of Classification Search
USPC .......... 204/400, 403.01, 424–432; 422/82.01, 422/82.03; 73/23.31–23.33
See application file for complete search history.

(56) References Cited

U.S. PATENT DOCUMENTS

| | | | |
|---|---|---|---|
| 5,173,166 A | 12/1992 | Tomantschger | |
| 5,302,274 A | 4/1994 | Tomantscbger | |
| 5,744,697 A | 4/1998 | Martell | |
| 5,777,208 A | 7/1998 | Martell | |
| 5,827,948 A | 10/1998 | Martell | |
| 5,914,019 A | 6/1999 | Dodgson | |
| 5,987,965 A | 11/1999 | Martell | |
| 6,099,708 A | 8/2000 | Mallory | |
| 6,129,825 A | 10/2000 | Mallory | |
| 6,305,214 B1 | 10/2001 | Schattke | |
| 6,741,221 B2 | 5/2004 | Aisenbrey | |
| 6,947,012 B2 | 9/2005 | Aisenbrey | |
| 7,060,652 B2 | 6/2006 | Gollar, III | |
| 7,077,936 B2 * | 7/2006 | Saito et al. | 204/192.2 |
| 7,223,469 B2 | 5/2007 | Aisenbrey | |
| 2007/0204460 A1 | 9/2007 | Aisenbrey | |

FOREIGN PATENT DOCUMENTS

| | | |
|---|---|---|
| GB | 2444136 A | 5/2008 |
| WO | WO0131327 A1 | 5/2001 |

OTHER PUBLICATIONS

Cao, Z. and Stetter, J.R., "The Properties and Applications of Amperometric Gas Sensors," Electroanalysis, 4(3), 253 (1992).

* cited by examiner

*Primary Examiner* — Alex Noguerola
(74) *Attorney, Agent, or Firm* — Bartony & Associates, LLC

(57) ABSTRACT

An electrochemical sensor includes a polymeric housing and at least a first electrode within the housing. The first electrode includes an electrochemically active surface. The electrochemical sensor further includes a first connector in electrically conductive connection with the first electrode. The first connector includes a first extending member formed from a conductive loaded polymeric material. The first extending member is formed such that an interior thereof comprises conductive elements within a matrix of the polymeric material so that the interior is electrically conductive and an exterior surface thereof comprises the polymeric material and is less conductive than the conductive interior. The conductive interior of the first extending member is in electrically conductive connection with the first electrode. The first connector further includes a first extending conductive element in electrical connection with the conductive interior. The first extending conductive element extends from the first extending member to pass through the polymeric housing. A sealing bond is formed between the polymeric material of the first extending member and the polymeric housing. The first extending conductive element can, for example, pass through the exterior surface of the first extending member.

18 Claims, 8 Drawing Sheets

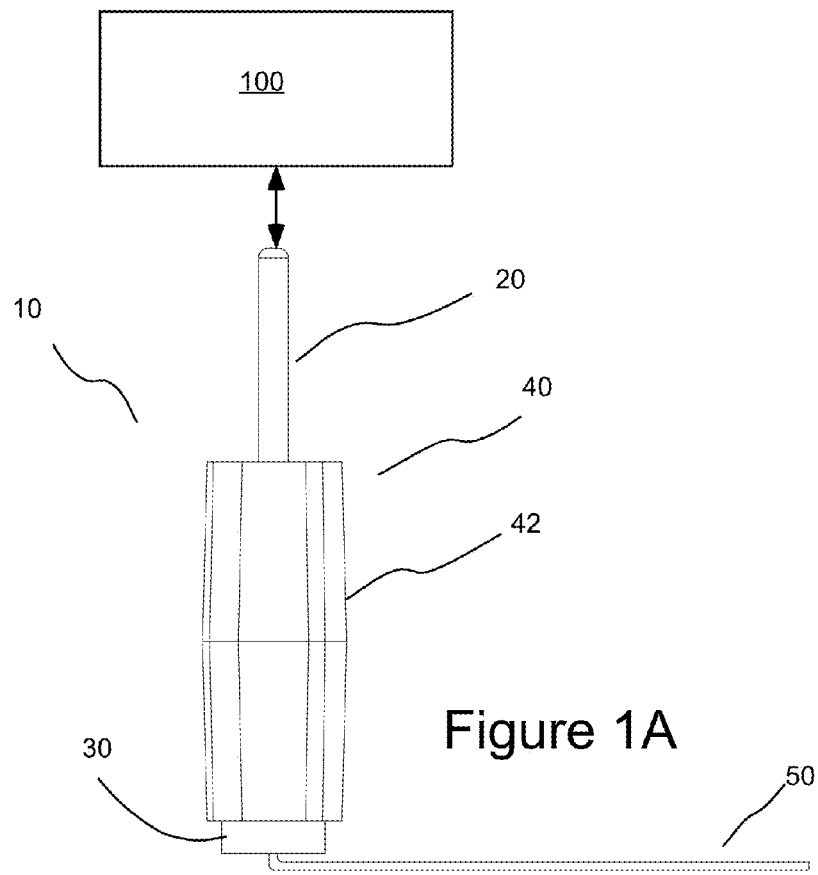
Figure 1A
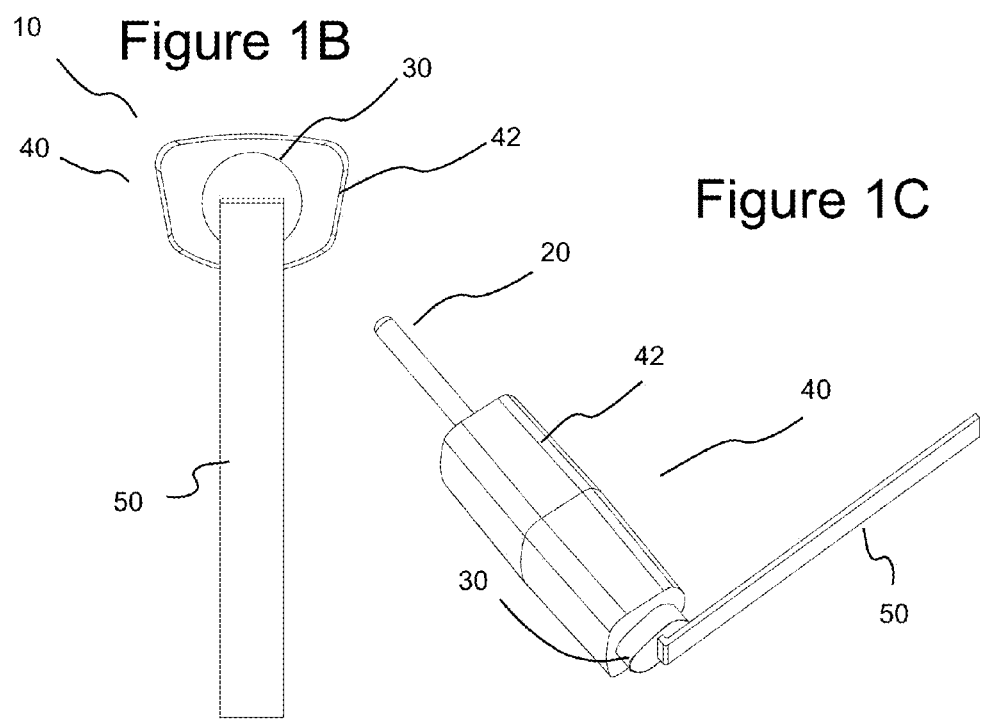
Figure 1B
Figure 1C

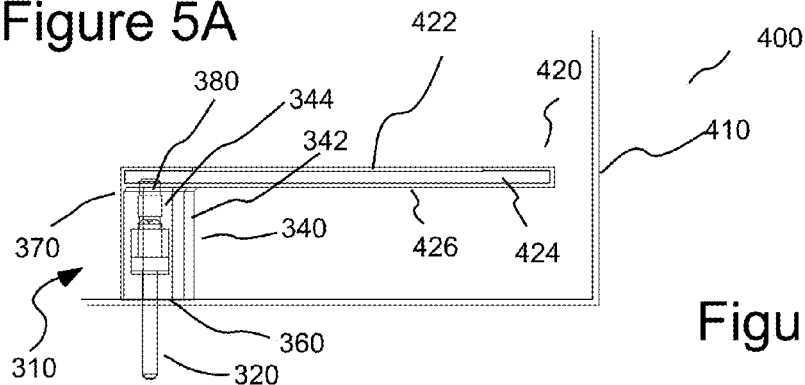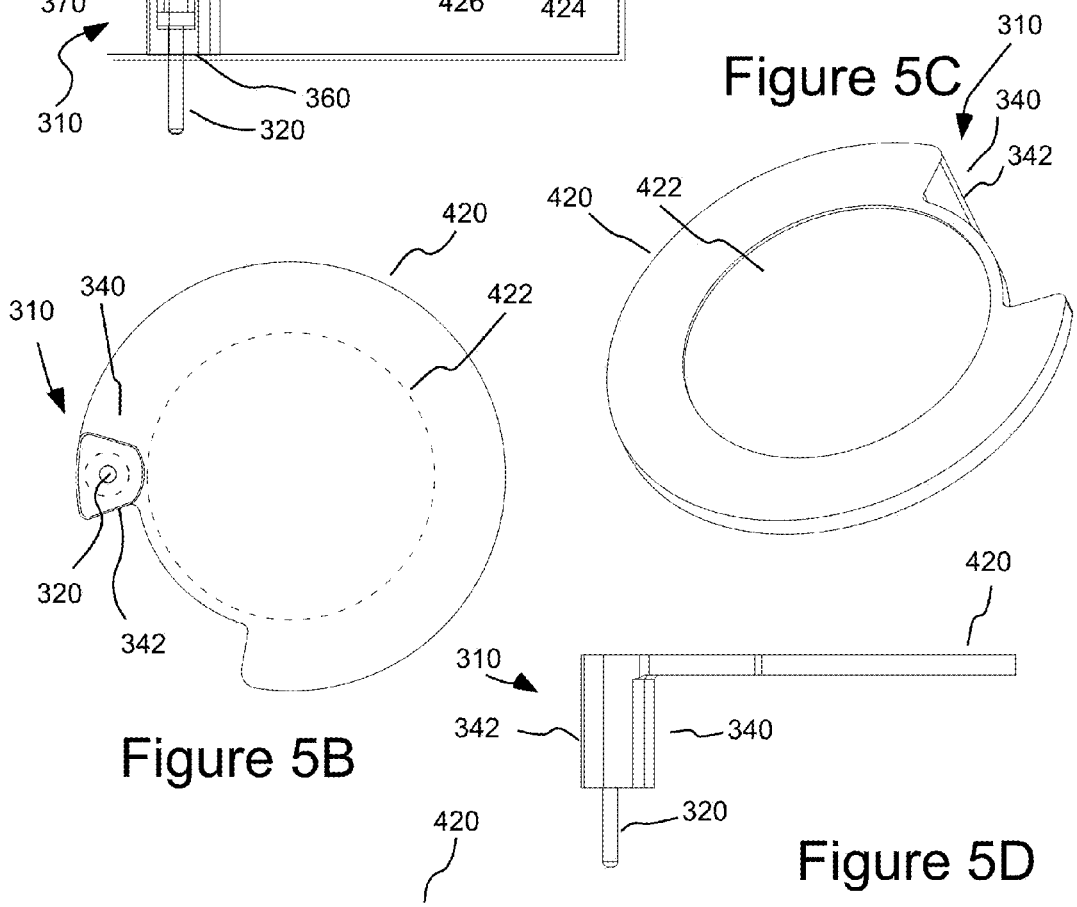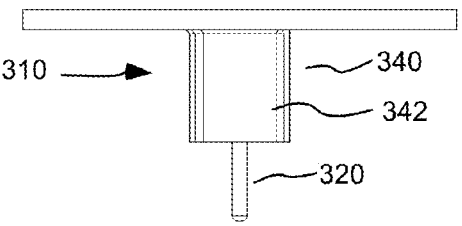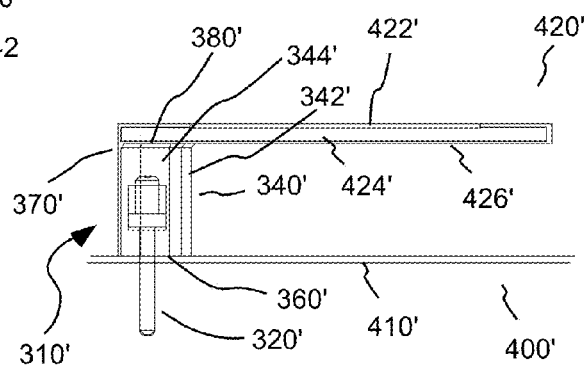

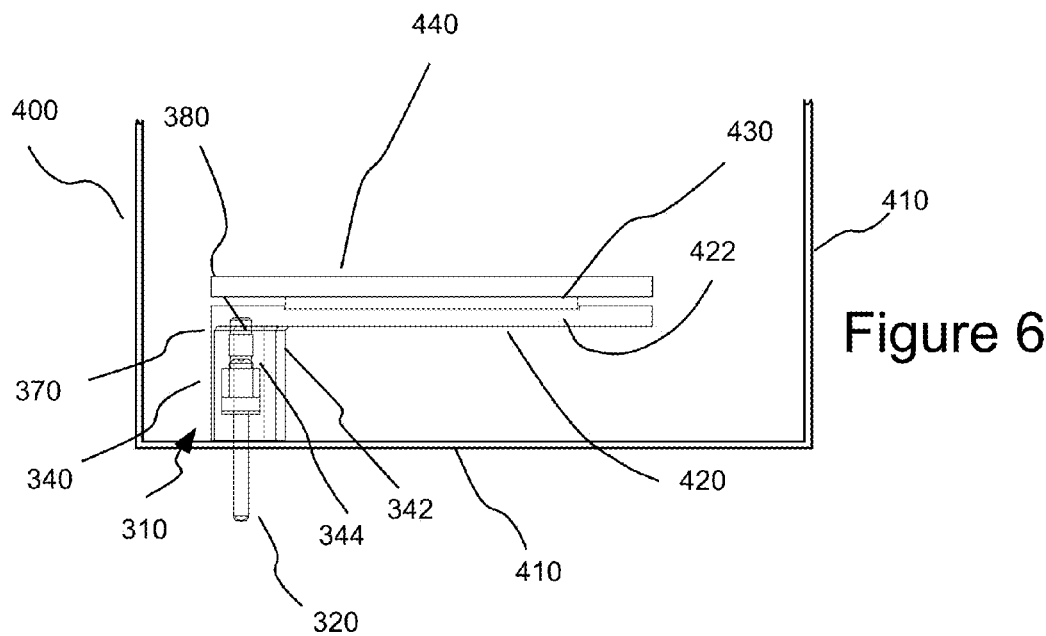
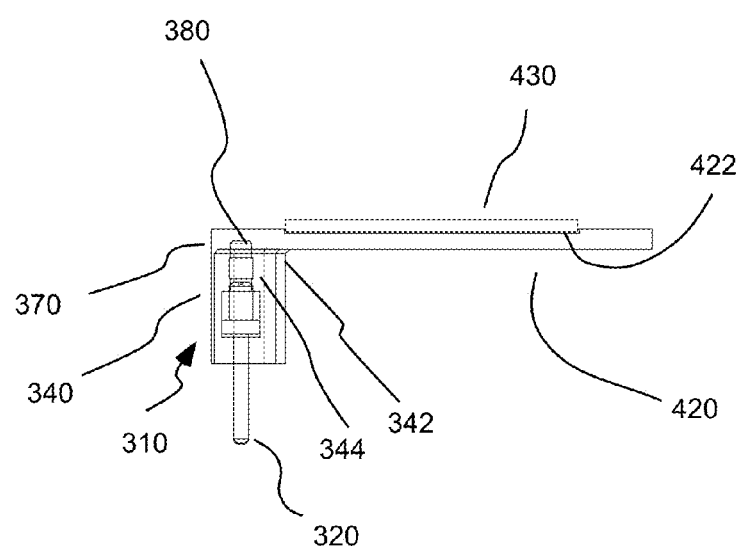

SENSORS AND SENSOR HOUSING SYSTEMS

BACKGROUND OF THE INVENTION

The present invention relates to sensors for the detection of gas analytes and to sensor housing systems and, particularly, to electrochemical gas sensors and housing systems therefor.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

Amperometric electrochemical gas sensors are electrochemical cells similar in structure and operation to batteries and fuel cells. As such, these three devices have several structures in common. In that regard, such devices include an anode, or anode compartment, where electrochemical oxidation occurs, a cathode, or cathode compartment, where electrochemical reduction occurs, an ionically conductive electrolyte, which maintains ionic electrical contact between the two electrodes, a housing, to enclose the electrodes and electrolyte, and contacts or poles, which are generally metallic electrical contacts between the electrodes and an external electronic circuitry used in connection with the devices. Batteries and fuel cells function primarily as power sources and place few design restrictions on the circuitry to which they may be in electrical contact. Amperometric gas sensors often require the use of specific driving circuitry, generally referred to as a potentiostat, for proper function. However, there are amperometric gas sensors that function analogously to fuel cells, and only require a method of measuring the electrical current which flows between the anode and cathode in the presence of the target analyte gas.

In an electrochemical gas sensor, the gas to be measured typically passes from the atmosphere into the sensor housing through a gas porous or gas permeable membrane to a first electrode known as a working electrode (sometimes called a sensing electrode) where a chemical reaction occurs. A complementary chemical reaction occurs at a second electrode known as a counter electrode (or an auxiliary electrode). The electrochemical sensor produces an analytical signal via the generation of a current arising directly from the oxidation or reduction of the analyte gas (that is, the gas to be detected) at the working and counter electrodes. A comprehensive discussion of electrochemical gas sensors is also provided in Cao, Z. and Stetter, J. R., "The Properties and Applications of Amperometric Gas Sensors," *Electroanalysis,* 4(3), 253 (1992), the disclosure of which is incorporated herein by reference.

To be useful as an electrochemical sensor, a working and counter electrode combination must be capable of producing an electrical signal that is (1) related to the concentration of the analyte gas and (2) sufficiently strong to provide a signal-to-noise ratio suitable to distinguish between concentration levels of the analyte gas over the entire range of interest. In other words, the current flow between the working electrode and the counter electrode must be measurably proportional to the concentration of the analyte gas over the concentration range of interest.

In addition to a working electrode and a counter electrode, an electrochemical sensor often includes a third electrode, commonly referred to as a reference electrode. A reference electrode is used to maintain the working electrode at a known voltage or potential. The reference electrode should be physically and chemically stable in the electrolyte.

Electrical connection between the working electrode and the counter electrode is maintained through an electrolyte. Important functions of the electrolyte include: (1) to efficiently carry the ionic current; (2) to solubilize the analyte gas; (3) to support both the counter and the working electrode reactions; and (4) to form a stable reference potential with the reference electrode. Important criteria for an electrolyte include the following: (1) electrochemical inertness; (2) ionic conductivity; (3) chemical inertness; (4) temperature stability; (5) low cost; (6) low toxicity; (7) low flammability; and (8) appropriate viscosity.

In general, the electrodes of an electrochemical cell provide a surface at which an oxidation or a reduction reaction occurs to provide a mechanism whereby the ionic conduction of the electrolyte solution is coupled with the electron conduction of the electrode to provide a complete circuit for a current.

The measurable current arising from the cell reactions of the electrochemical cell is directly proportional to the extent of reaction occurring at the electrode. Preferably, therefore, a high reaction rate is maintained in the electrochemical cell. For this reason, the counter electrode and/or the working electrode of the electrochemical cell generally comprise an appropriate electrocatalyst on the surface thereof to support the reaction rate.

Batteries are completely self-contained electrochemical energy storage and conversion devices. They are arranged so that both the anode and the cathode are comprised of or are in intimate electrical contact with relatively large quantities of substances with sufficiently different electrochemical energies such that when the anode and cathode poles are connected to electronic circuitry, significant and useful amounts of electrical current flow through the circuitry. The source of this current is the electrochemical conversions of the anode and cathode materials (oxidation and reduction). Thus, batteries are a useful electrochemical device. Batteries are entirely self-contained from an electrochemical point of view in that they are fabricated with sufficient anode and cathode material to provide a useful lifetime or amount of electrical energy. As such, batteries are usually well sealed. In many designs, they are hermetically sealed. Common examples of batteries include the Leclanche' cell (the 'dry' cell) and the Plante' cell (the lead acid battery).

Fuel cells, on the other hand, are electrochemical energy conversion devices that require an external supply of the anode material, the cathode material or both. The electrodes of fuel cells are usually electrocatalytic in nature (that is, they provide electrochemically active surfaces to support the electrochemical reactions, but do not actually chemically participate in them). Unlike batteries, for which the useful life generally ends when the electrochemically active electrode materials are consumed, a fuel cell will operate continuously as long as electrochemically active fuel (anode material) and oxidizer (cathode material) are supplied to the device. A common fuel cell is the Grove cell, or hydrogen-oxygen fuel cell. In that fuel cell, hydrogen is the fuel and oxygen is the oxidizer.

Amperometric electrochemical gas sensors can be considered special cases of fuel cells in that they are typically miniature cells (compared to power generation fuel cells) that are designed to use a target gas or analyte gas (that is, a gas of analytical interest) as the fuel. In the absence of the target gas, there are no bulk electrochemical conversions (Faradaic reactions) occurring at the electrodes of the sensor and, hence, essentially zero current flows in the sensor. When present, the target gas undergoes electrochemical oxidation or reduction as described above, with corresponding generation of Faradaic currents. The resultant current flow is sensed by the external driving circuitry and is the analytical signal of the sensor. Once again, the observed current is typically directly proportional to the concentration of the analyte gas present.

Although batteries, fuel cells and amperometric electrochemical gas sensors are very similar, the manufacture of amperometric gas sensors poses several unique difficulties. First, unlike batteries, there must be a gas entry to allow the ingress of the analyte gas. There must also be contacts or poles which carry the current from the surfaces of the electrodes to the external circuitry. Finally, the sensor must be fabricated in such a way as to retain the ionic electrolyte, often a highly corrosive aqueous acid or base. Methods and systems for sealing such sensors against leakage of the internal liquid electrolyte while allowing entry of the analyte gas and collection of the resultant currents are an important feature of the mechanical design of such sensors.

Sealing methods in currently available amperometric electrochemical gas sensors include compressible o-rings, adhesives, sealants, even battery-type housings, either individually or in combination. Generally, the electrochemical gas sensors also include an electronic current path to carry the analytical currents generated at the electrodes to the external circuitry. Such electronic current paths typically take the form of metallic pins, wires or ribbons that penetrate the sensor housing to carry the current from the electrodes. Such metallic element provide a pathway for leakage over the lifetime of the sensor.

Electrically conductive plastics have been used to form all or part of a sensor housing in an attempt to provide an efficient electrical current path from the electrode surfaces to the external circuitry without creating a potential leak path from the interior of the sensor housing. Such conductive plastics are generally homogeneous with respect to conductivity in that they exhibit conductivity throughout an article, component or part formed from the conductive plastic. Such plastics enable conduction of electricity from the inside of a sensor housing to the outside. Conductive plastics portions have, for example, been insert injection molded into typical plastic sensor housings and have been incorporated into the sensor housing by adhesives, welding, heating, etc. The conductive portions of the sensor housing serve both to carry current from the electrodes of the sensor to the external circuitry and to form part of the structure and sealing system of the sensor. The conductive polymers or plastics used in sensors can be relatively expensive and difficult to use in manufacturing procedures.

Although there have been a number of methods and systems developed to form electronic current paths from electrodes within an electrochemical sensor, it is desirable to develop improved methods and systems of providing such electronic current paths.

SUMMARY OF THE INVENTION

In one aspect, an electrochemical sensor for the detection of an analyte is provided. The electrochemical sensor includes a polymeric housing and at least a first electrode within the housing. The first electrode includes an electrochemically active surface. The electrochemical sensor further includes a first connector in electrically conductive connection with the first electrode. The first connector includes a first extending member formed from a conductive loaded polymeric material. The first extending member is formed such that an interior thereof comprises conductive elements within a matrix of the polymeric material so that the interior is electrically conductive and an exterior surface thereof comprises the polymeric material and is less conductive than the conductive interior. The conductive interior of the first extending member is in electrically conductive connection with the first electrode. The first connector further includes a first extending conductive element in electrical connection with the conductive interior. The first extending conductive element extends from the first extending member to pass through the polymeric housing. A sealing bond is formed between the polymeric material of the first extending member and the polymeric housing. The first extending conductive element can, for example, pass through the exterior surface of the first extending member.

In a number of embodiments, at least a portion of the exterior surface of a first position of the first extending member is removed to expose the conductive interior of the first extending member at the first position thereof to form electrically conductive connection with the first electrode. The first extending conducting element can be spaced from the first position so that an electrically conductive pathway between the first extending conducting element and the first position passes through the conductive interior of the first extending member.

In several embodiments, the electrochemical sensor further includes a second extending conducting element in electrical connection with the conductive interior. The second extending conducting element is in electrically conductive connection with the first electrode. The first extending conducting element can be spaced from the second extending conducting element within the conductive interior so that an electrically conductive pathway between the first extending conducting element and the second extending conducting element passes through the conductive interior of the first extending member.

In several embodiments, the first electrode is formed from a conductive loaded polymeric material such that an interior thereof comprises conductive elements within a matrix of the polymeric material so that the interior is electrically conductive and an exterior surface thereof comprises the polymeric material and is less conductive than the interior. The conductive interior of the first electrode is placed in electrical connection with the first extending conducting element via the conducting interior of the first extending member.

At least a portion of the exterior surface of a first position of the first extending member can, for example, be removed to expose the conductive interior of the first extending member at the first position thereof to form electrically conductive connection with a first portion of the first electrode from which the exterior surface of the first electrode has been removed to expose the conductive interior of the first electrode. As described above, the first extending conducting element can be spaced from the first position so that an electrically conductive pathway between the first extending conducting element and the first position passes through the conductive interior of the first extending member.

The electrochemical sensor can also further include a second extending conducting element in electrical connection with the conductive interior of the first extending member. The second extending conducting element can be in electrically conductive connection with the first electrode. As described above, the first extending conducting element can be spaced from the second extending conducting element within the conductive interior of the first extending member so that an electrically conductive pathway between the first extending conducting element and the second extending conducting element passes through the conductive interior of the first extending member.

An electrocatalytic material can be placed in electrically conductive contact with the conductive interior of the first electrode.

The polymeric material of the first connector, the polymeric material of the first electrode and a polymeric material of the housing can, for example, be the same polymeric material.

The first extending conductive element can, for example, include a metal.

In several embodiments, the electrochemical sensor further includes at least a second electrode and a second connector in electrically conductive connection with the second electrode. The second connector includes a second extending member formed from a conductive loaded polymeric material. The second extending member is formed such that an interior thereof comprises conductive elements within a matrix of the polymeric material so that the interior is electrically conductive and an exterior surface thereof comprises the polymeric material and is less conductive than the conductive interior of the second extending member. The conductive interior of the second extending member is in electrically conductive connection with the second electrode. The second connector further includes a first extending conductive element in electrical connection with the conductive interior of the second extending member. The first extending conductive element of the second connector extends from the second extending member to pass through the polymeric housing. A sealing bond is formed between the polymeric material of the second extending member and the polymeric housing.

The electrochemical sensor can further include at least a third electrode and a third connector in electrically conductive connection with the third electrode. The third connector includes a third extending member formed from a conductive loaded polymeric material. The third extending member is formed such that an interior thereof comprises conductive elements within a matrix of the polymeric material so that the interior is electrically conductive and an exterior surface thereof comprises the polymeric material and is less conductive than the conductive interior of the third extending member. The conductive interior of the third extending member is in electrically conductive connection with the third electrode. The third connector further includes a first extending conductive element in electrical connection with the conductive interior of the third extending member. The first extending conductive element of the third connector extends from the third extending member to pass through the polymeric housing. A sealing bond is formed between the polymeric material of the third extending member and the polymeric housing.

In a number of embodiments, the first electrode is a working electrode, the second electrode is a counter electrode and the third electrode is a reference electrode.

In another aspect, a system includes a polymeric housing and a first connector in electrically conductive connection with a first component within the housing. The first connector includes a first extending member formed from a conductive loaded polymeric material. The first extending member is formed such that an interior thereof includes conductive elements within a matrix of the polymeric material so that the interior is electrically conductive and an exterior surface thereof comprises the polymeric material and is less conductive than the conductive interior. The conductive interior of the first extending member is in electrically conductive connection with the first component. The first connector further includes a first extending conductive element in electrical connection with the conductive interior of the first extending member. The first extending conductive element extends from the first extending member to pass through the polymeric housing. A sealing bond is formed between the polymeric material of the first extending member and the polymeric housing.

In a further aspect, a method of providing for electrically conductive connection between a first component within a polymeric housing to a second component outside of the polymeric housing, includes: placing a first connector in electrically conductive connection with the first component, the first connector including a first extending member formed from a conductive loaded polymeric material, the first extending member being formed such that an interior thereof includes conductive elements within a matrix of the polymeric material so that the interior is electrically conductive and an exterior surface thereof comprises the polymeric material and is less conductive than the conductive interior, the conductive interior of the first extending member being placed in electrically conductive connection with the first component, the first connector further including a first extending conductive member in electrical connection with the conductive interior of the first extending member; passing the first extending conductive element through a passage in the polymeric housing; forming a sealing bond between the polymeric material of the first extending member and the polymeric housing, and placing the first extending conductive element in electrically conductive connection with the second component.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 1A illustrates a side, partially transparent view of a current path structure, current path system or connector of the present invention.

FIG. 1B illustrates an end view of the connector of FIG. 1A.

FIG. 1C illustrates a perspective view of the connector of FIG. 1A.

FIG. 5A illustrates a side, partially transparent view of a portion of a sensor of the present invention including an electrode support of an electrode or electrode structure, system or assembly in electrical connection with a connector.

FIG. 5B illustrates a partially transparent end view of the electrode support and the connector of FIG. 5A.

FIG. 5C illustrates a perspective view of the electrode support and the connector of FIG. 5A.

FIG. 5D illustrates another side view of the electrode support and the connector of FIG. 5A.

FIG. 5E illustrates another side view of the electrode support and the connector of FIG. 5A.

FIG. 5F illustrates a side, partially transparent view of a portion of another sensor of the present invention including an electrode support of an electrode or electrode structure, system or assembly in electrical connection with a connector, wherein an electrically conductive interior of the connector is placed in direct electrical connection with an electrically conductive interior of the electrode support.

FIG. 6 illustrates a side, partially transparent view of a portion of a sensor of the present invention including an electrode support of an electrode in electrical connection with a connector, wherein an electrocatalytic material immobilized upon a support is in electrical connection with a conductive portion of the electrode support.

FIG. 7 illustrates a side, partially transparent view of a portion of a sensor of the present invention including an electrode support in electrical connection with a connector, wherein an electrocatalytic material is immobilized directly upon a conductive portion of the electrode support.

DETAILED DESCRIPTION OF THE INVENTION

Figure 2:
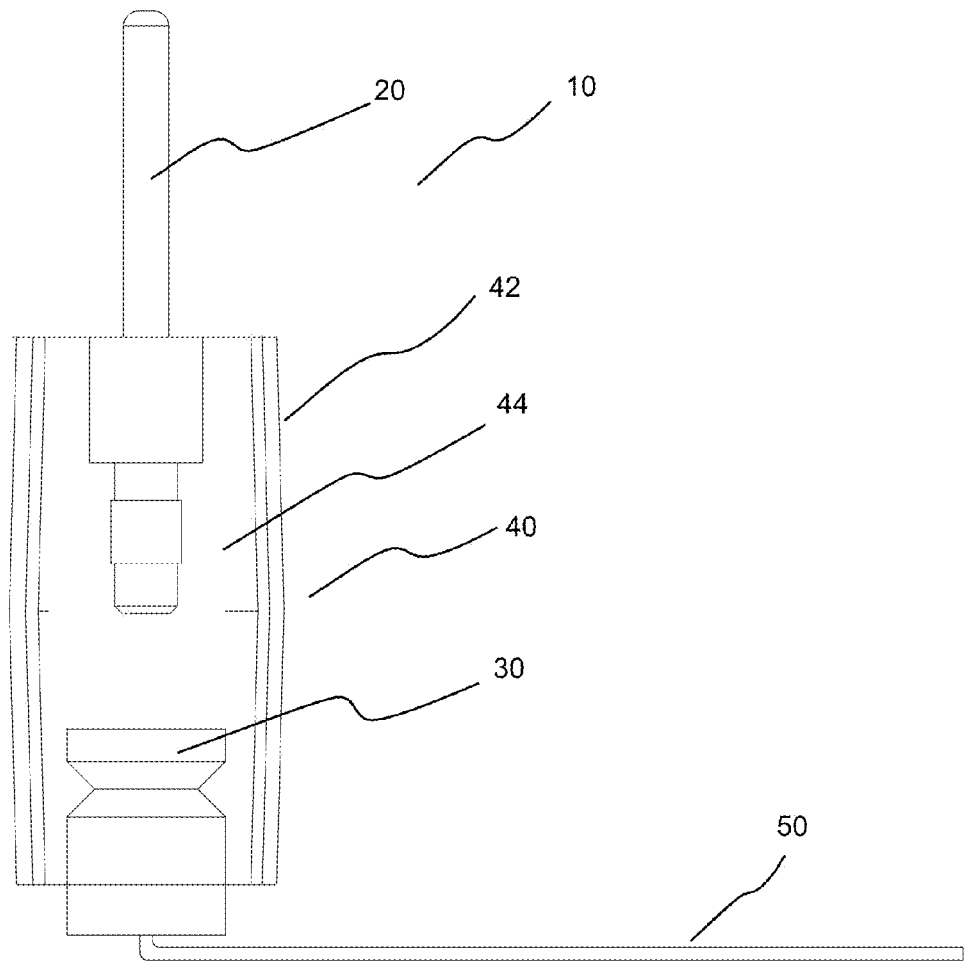
FIG. 2 illustrates a side, cutaway view of the connector of FIG. 1A.

As used herein and in the appended claims, the singular forms "a," "an", and "the" include plural references unless the context clearly dictates otherwise. Thus, for example, reference to "a pin or post" includes a plurality of such pins or posts and equivalents thereof known to those skilled in the art, and so forth, and reference to "the pin or the post" is a reference to one or more such pins or posts and equivalents thereof known to those skilled in the art, and so forth.

Conductive plastics that have previously been used in electrochemical gas sensors to transmit electrical current exhibit both bulk and surface conductivity. Unlike the conductive polymers or plastics previously used in electrochemical gas sensors, the conductive polymers or plastics used in the electrochemical gas sensors of the present invention exhibit bulk conductivity properties, but surface insulating properties. In that regard, the surface conductivity of the conductive polymers used in the electrochemical gas sensors of the present invention is approximately zero, that is, essentially identical to the base plastic from which the conductive portions are molded. However, the internal structure of the polymer has very high electrical conductivity, similar to that of metals.

A polymer-based material suitable for use in the electrochemical gas sensors of the present invention is available from Integral Technologies, Inc. of Bellingham, Wash. USA and is sold under the trade name ELECTRIPLAST™. The ELECTRIPLAST material includes a polymeric (for example, a thermoplastic polymeric) resin into which has been incorporated electrically conductive elements such as metallic fibers and/or powders. Such compositions are discussed, for example, in U.S. Pat. Nos. 7,223,469, 6,947,012, 6,741,221 and U.S. Patent Application Publication No. 2007/0204460. As a result of processing (for example, injection molding) of resin pellets including the thermoplastic polymer and the conductive elements, the conductive elements form a conductive network within the structure of the processed part. However, as a result of the initial structure of the resin pellets and control of processing parameters, the surfaces of the processed/molded parts have no little or no exposed metal fibers, and are not significantly conductive. Thus, unlike a pure metal such as copper or aluminum, the surface of the processed/molded parts is ether non-conductive or has a significantly lower conductivity than that measured through the core of the part. This unique property results from the combination of non-conductive, polymeric resin and conductive additive/fibers and the uneven distribution of the conductive additives/fibers throughout the processed/molded part. During the injection molding process, the relatively large (on a molecular scale) conductive additives, such as metal or carbon fibers, are affected by the levels of shear between the additives/fibers and the molding compounds. This process leads to uneven distribution of the conductive material inside the part, particularly around part features such as sharp corners, openings, and at the outer skin of the part. By adjusting mold parameters, it is possible to mold a part that has all or almost all of the conductive additives/fibers at the interior or core of the part and to form a non-conductive or substantially non-conductive skin. The exterior portion or surface of the part can be formed to be sufficiently non-conductive to operate as an electrical insulator for the conductive interior, substantially or completely preventing flow of electric current thereacross.

To make electrical contact with the internal, conductive portion or core of, for example, an injection molded part; a conductor (for example, a metallic conductor) can be inserted into the interior of the part, or the surface insulating layer of thermoplastic polymer can be removed (for example, mechanically or chemically), thereby exposing the conductive portion of the part.

FIGS. 1A through 2 illustrate a representative example of a connector structure, connector system or connector 10, wherein a first extending conductive element in the form of a contact pin or post 20 and a second extending conductive element in the form of contact pin or post 30 are, for example, insert molded into opposite ends of an extending structure or member 40 formed to have an non-conductive or insulating surface layer 42 and a conductive internal portion, core or interior 44 (radially inward from surface 42) as described above. Pins 20 and 30 can, for example, be metallic pins or posts so that connector 10 has two metallic, conductive contacts at each end of injection molded extending member 40. One contact, pin 20 can, for example, serve to make electrical contact to electronic circuitry 100 (represented schematically in FIG. 1A). The other contact, pin or post 30, can, for example, be used to make contact with a sensor electrode within a sensor housing (not shown in FIGS. 1A through 2), either directly or through the use of a contact ribbon or wire 50, which can be attached (for example, welded) to post 30. Pin 20 can, for example, be a commercially available contact pin, fabricated from a base metal and coated with a standard solderable coating. Pin or post 30 can, for example, be a contact member specifically fabricated as known in the sensor arts from materials known to be electrically and chemically compatible with the ionic electrolyte of the sensor and unaffected by Faradaic processes that occur in the sensor as a result of its operation.

Referring to FIG. 1B, the area immediately adjacent to and surrounding pin 30 on the end of extending member 40 is electrically insulating, as is entire surface 42 of the injection molded, internally conductive thermoplastic extending member 40. In several embodiments, insulating surface 42 is chemically similar or the same as the sensor housing (which can, for example, be injection molded), affording a mechanism to create a molecular bond or weld between thermoplastic connector 10 and the thermoplastic sensor housing. In this manner, a leak tight seal is formed between the two plastic structures, through which passes external electrical contact pin 20.

In the embodiment of FIGS. 1 and 2, the ends of pin 20 and post 30 within conductive core or interior 44 are spaced so that a so that an electrically conductive pathway between the pin 20 and post 30 passes through conductive interior 44 of connector 10. Separation of pin 20 and post 30 substantially reduces the potential for formation of a pathway through connector 10 for leakage of, for example, electrolyte through connector 10. The polymer matrix of connector 10 provides a seal between pin 20 and post 30, while the conductive elements concentrated within conductive interior 44 provide a conductive pathway therebetween. In the case of previous electrical connectors including conductive metallic elements within polymeric, insulating materials, the extending interface between the conductive element and the polymeric insulating material provided a pathway for leakage over the lifetime of the sensor. In the case of the conductive polymeric materials of connector 10, there is no such extending or continuous interface or pathway for leakage.

Figure 3:
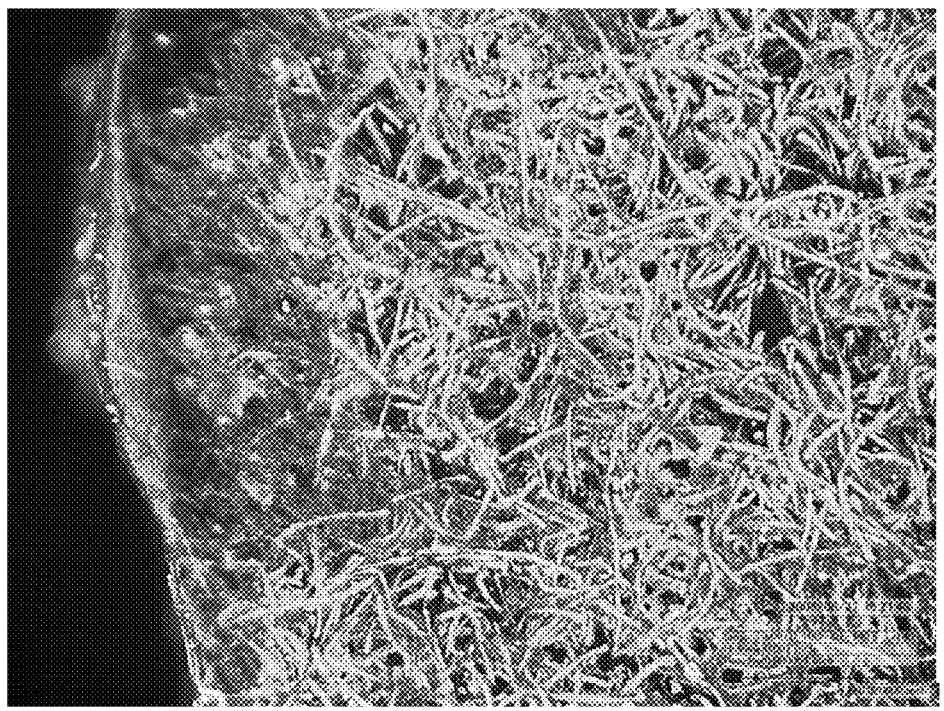
FIG. 3 illustrates a photomicrograph of an injection molded thermoplastic composite component, wherein an insulating surface layer has been removed by chemical etching.

FIG. 3 illustrates a photomicrograph of an injection molded thermoplastic composite component of the present invention wherein the insulating surface layer has been removed by chemical etching. The metallic element (for example, metallic fibers), which render the structure internally conductive, are illustrated.

Figure 4:
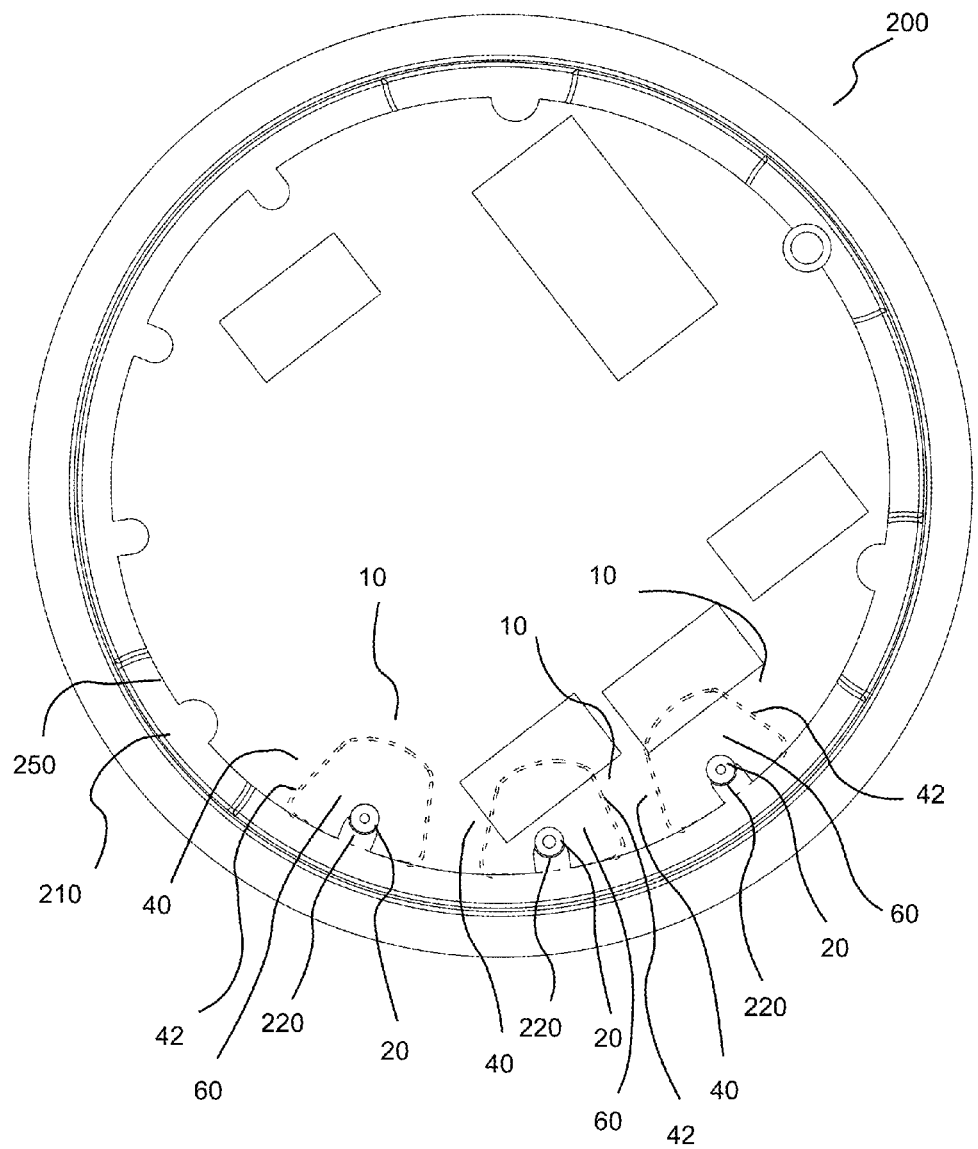
FIG. 4 illustrates a bottom, partially transparent view of a sensor including several connectors of FIG. 1A.

FIG. 4 illustrates a partially transparent bottom view of sensor 200 in which connector 10 is assembled into a housing 210 of sensor 200. In the illustrated embodiment, the extending pin portion of pin 20 extends through a passage or hole 220 in sensor housing 210 to be placed in electronic connection with to electronic circuitry external to sensor housing 210. Electronic circuitry external to housing 210 of sensor 200 can, for example, include a printed circuit board 250 attached to the bottom of housing 210.

An end surface or area 60 surrounding pin 20 becomes a sealing surface between sensor housing 210 and connector 10. Because end surface 60 of extending member 40 is similar or generally the same in composition to the thermoplastic surface of sensor housing 210, a leakproof seal can be easily created between the two structures. Such a leakproof seal or bond can be accomplished in a number of ways, including, for example, via adhesives, solvent welding, heat staking, friction welding, laser welding, etc.

The conductive thermoplastic polymeric material of extending member 40, as stated above, is fabricated from an admixture of a polymeric material (for example, a thermoplastic resin) and conductive elements such as conductive fibers. The conductive elements can, for example, be metallic in nature and can be chosen from common electrical conductors such as copper, silver, gold, nickel, or stainless steel. Carbon fiber, either native or coated with a metal such as copper or nickel, can also be used. Furthermore, nanotubes such as single or multiwalled carbon nanotubes may also be used to impart electrical conductivity to the thermoplastic. An example of suitable carbon nanotubes are BAYTUBES™ available from Bayer MaterialScience AG of Leverkusen, Germany.

A portion or another embodiment of a sensor 400 of the present invention is illustrated in FIGS. 5A through 5E. In the embodiment of FIGS. 5A through 5E, an injection molded, current carrying connector 310 is formed of conductive plastic as described above. A first extending conductive element or contact pin 320 is, for example, molded within an extending member 340. As described above in connection with pin 20, extending pin 320 can, for example, be a commercially available electrical contact pin. As described in connection with FIG. 4, insulating, generally flat, first end surface 360 around pin 320 serves as a sealing surface wherein a molecular seal or molecular bond is formed between a thermoplastic sensor housing 410 (a portion of which is represented schematically in FIG. 5A) and the internally electrically conductive thermoplastic extending member 340 of structure 310.

In several embodiments, electrode support 420 is also made of the same or a similar electrically conductive polymeric material as connector 310. In that regard, electrode support 420 includes an internal, electrically conductive core or interior 424 including conductive elements as described above and an insulating exterior 426 (see FIG. 5A). In the embodiment of FIGS. 5A through 5E, a second extending conductive element or contact post 380 extends from a second end 370 of connector 310 to extend through insulating exterior surface 426 of electrode support 420 to form an electrical connection with conductive core or interior 424. Second end 370 can, for example, be bonded to exterior surface 426 to form a seal therebetween.

In another embodiment illustrated in FIG. 5F, a second end 370' of (internally electrically conductive) structure 340' includes a contact portion 380'. In that regard, at second end 370', the nonconductive surface 342' of extending member 340' is removed to expose the conductive element/fibers embedded in conductive interior 344' of extending member 340' (see FIG. 3). The exposing of conductive interior 344' at second end 370' can be accomplished in a variety of ways, including, but not limited to, mechanical operation, chemical etching, and/or surface ablation. Once insulating surface 342' of second end 370' is removed, the internal conductive elements are available for electrical connection with an electrode support 420' of an electrode of sensor 400'. In the area of contact of electrode support 420' with contact portion 380' of connector 310', the internal conductive elements of electrode support 420' are exposed or made available for electrical connection with contact portion 380'. In respects other than the direct electrical contact of conductive interior 344' of connector 310 with conductive interior 424' of electrode support 420', sensor 400' is generally identical to sensor 400 and elements of sensor 400' are numbered similarly to corresponding elements of sensor 400 with the addition of the designation "'".

Referring once again to FIGS. 5A through 5E, electrode support 420, can for example, include a portion or section 422 wherein the internal conductive elements thereof are exposed. As illustrated in the embodiment of FIG. 6, the actual electrocatalytic material 430 of electrode support 420 can, for example, be immobilized upon (for example, adhered to) a secondary support membrane 440, which can, for example, include or be formed of a fibrous or porous mat that serves as a support structure and performs a wicking action necessary to keep the electrocatalytic electrode structure saturated with the liquid ionic electrolyte. Electrocatalytic portion 430 of the electrode structure, which is typically a noble metal such as platinum, iridium, palladium, or gold, can, for example, be pressed into intimate electrical contact with the exposed conductive fibers of conductive interior 424 in the area of portion 422 of electrode support 420.

Once again, a seal can be effected between extending member 340 (using the nonconductive thermoplastic surface adjacent to pin 320) and sensor 410 housing as described above. The totality of sensor 400 of FIG. 6 provides an electrocatalytic electrode or electrode structure, assembly or system in electrical contact with insert molded contact pin 320 of structure 310 through the internal conductive network of metal fibers molded within the structure 310. The composite structure or system serves the purposes of creating the internal electrocatalytic electrode of sensor 400, at which Faradaic reactions may occur as a function of gas sensing. In addition, a leakproof seal is created between extending connector 310 and sensor housing 410. Finally, pin 320 serves as the electrical contact to the external circuitry.

FIG. 7 illustrates another embodiment of the present invention, in which the electrocatalytic material or portion 430 is immobilized directly on the exposed conductive elements of portion 422 of electrode support 420. This immobilization can be accomplished in a variety of ways such as chemical vapor deposition or electroless deposition or electroplating. In this manner, all of the functions described above in connection with FIGS. 5A, 5F and 6 are created with fewer components.

Figure 8:
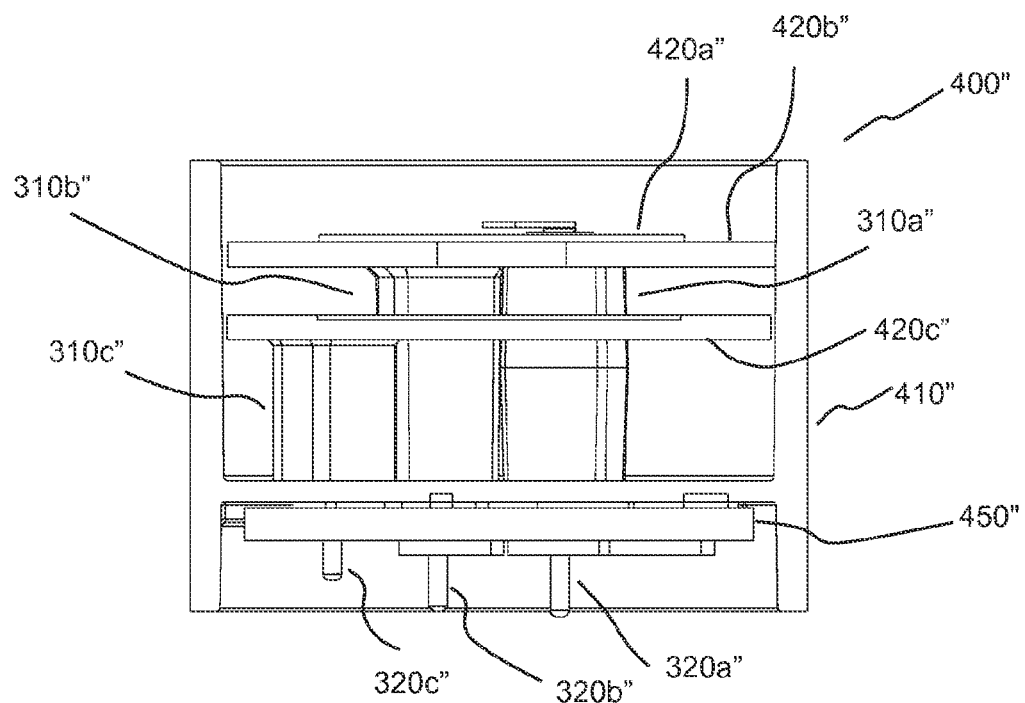
FIG. 8 illustrates a side cutaway view of a sensor of the present invention including a working electrode, a counter electrode and a reference electrode, each of which is in electrical connection with a connector of the present invention to place the electrodes in electrical connection with electronics external to the compartment in the sensor housing containing the electrolyte.

FIG. 8 illustrates a side cutaway view of sensor 400" including three electrodes (for example, a working electrode, a counter electrode and a reference electrode) within a housing 410". The electrodes can, for example, include electrode supports 420a", 420b" and 420c" which are fabricated from an electrically conductive polymeric material as described in connection with electrode support 420. As also described above, corresponding connectors 310a", 310b" and 310c" (which can, for example, be fabricated from the same or a similar conductive polymeric material as electrode supports 420a", 420b" and 420c") connect the electrode supports 420a", 420b" and 420c" with electronic circuitry exterior to housing 410". Electronic circuitry external to housing 410" of sensor 400" can, for example, include a printed circuit board 450" attached to the bottom of housing 410".

Experimental Section

In studies of several embodiments of the present invention, a number of sensors were constructed as illustrated in FIG. 4 to include a working electrode, a counter electrode and a reference electrode connected to electronic circuitry via connectors 10.

Figure 9A:
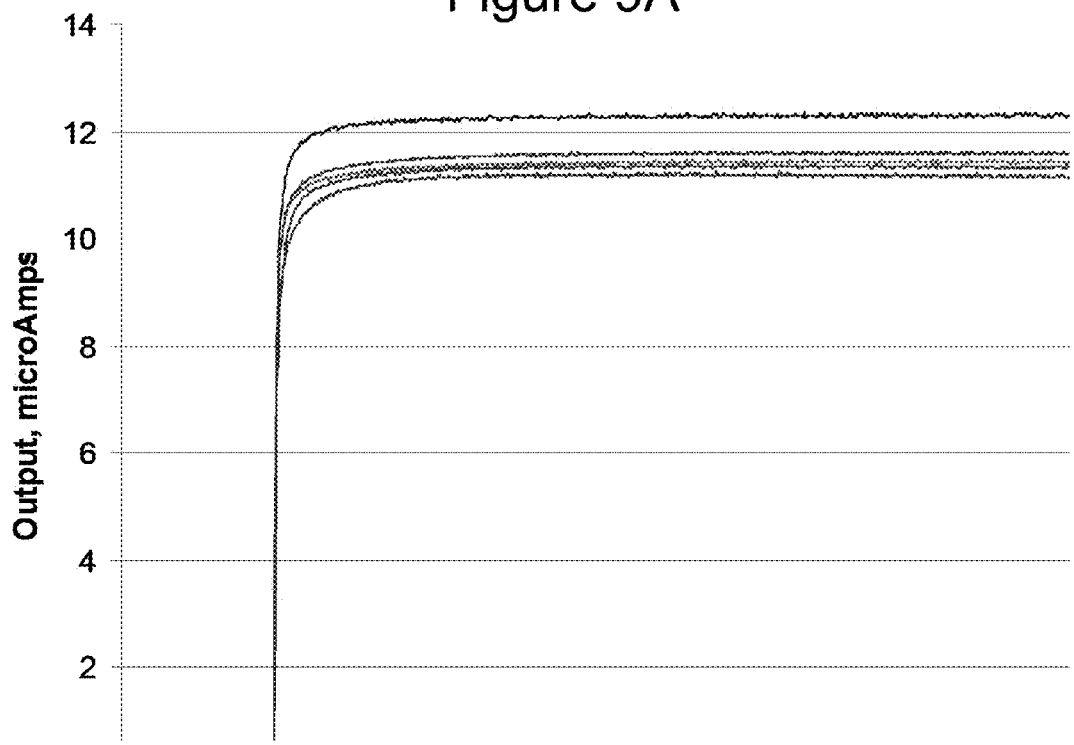
FIG. 9A illustrates a graph of sensor response to a 100 ppm carbon monoxide (CO) test gas for a sensor including a connector of FIG. 1A.

In, for example, carbon monoxide sensors of the present studies, the effective diffusion hole size of the sensors tested was a four-hole pattern of 0.0225 inch diameter per hole, and the sensors were tested under a 10Ω load with 100 ppm carbon monoxide at 250 cc/min. In the studies illustrated in FIG. 9A, the sensors were exposed to air for 2 min., then exposed to 100 ppm carbon monoxide for 10 min., and then exposed to air for 1 min. Under these conditions, an average sensor output of approximately 11.5 μAmp was achieved, with an average response time ($T_{90}$) of approximately 12 seconds and an average sensitivity of approximately 0.115 μAmp/ppm.

Figure 9B:
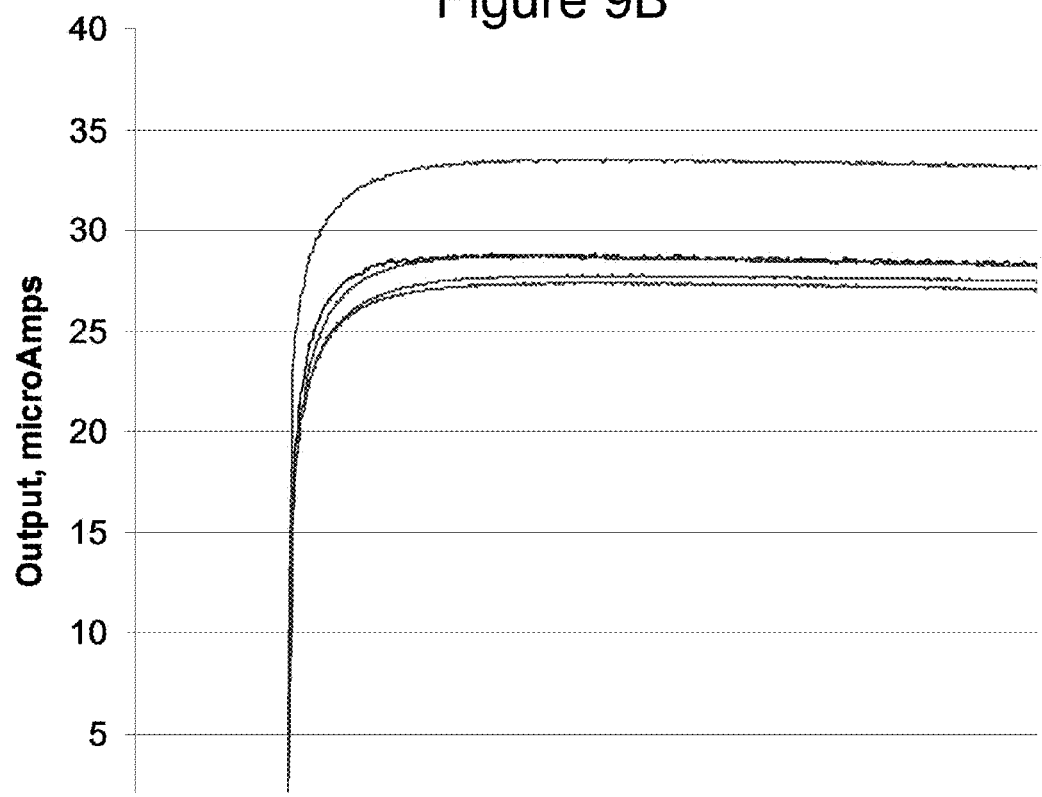
FIG. 9B illustrates a graph of sensor response to a 40 ppm hydrogen sulfide ($H_2S$) test gas for a sensor including a connector of FIG. 1A.

In the case of a hydrogen sulfide sensors of the present studies, the effective diffusion hole size of the sensors tested was 0.145 inch, and the sensors were tested under a 10Ω load with 40 ppm hydrogen sulfide at 250 cc/min. In the studies illustrated in FIG. 9B, the sensors were exposed to air for 2 min., then exposed to 40 ppm hydrogen sulfide for 10 min., and then exposed to air for 1 min. Under these conditions, an average sensor output of approximately 28.2 μAmp was achieved, with an average response time ($T_{90}$) of approximately 29 seconds and an average sensitivity of approximately 0.705 μAmp/ppm.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. An electrochemical sensor for the detection of an analyte, comprising: a polymeric housing, at least a first electrode within the housing, the first electrode comprising an electrochemically active surface, and a first connector in electrically conductive connection with the first electrode, the first connector comprising a first extending member formed from a conductive loaded polymeric material, the first extending member being formed such that an interior thereof comprises conductive elements within a matrix of the polymeric material so that the interior is electrically conductive and an exterior surface thereof comprises the polymeric material and is less conductive than the conductive interior, the conductive interior of the first extending member being in electrically conductive connection with the first electrode, the first connector further comprising a first extending conductive element in electrical connection with the conductive interior, the first extending conductive element extending from the first extending member to pass through the polymeric housing, a sealing bond being formed between the polymeric material of the first extending member and the polymeric housing.

2. The electrochemical sensor of claim 1 wherein the first extending conductive element passes through the exterior surface of the first extending member.

3. The electrochemical sensor of claim 1 wherein at least a portion of the exterior surface of a first position of the first extending member is removed to expose the conductive interior of the first extending member at the first position thereof to form electrically conductive connection with the first electrode.

4. The electrochemical sensor of claim 3 wherein the first extending conducting element is spaced from the first position so that an electrically conductive pathway between the first extending conducting element and the first position passes through the conductive interior of the first extending member.

5. The electrochemical sensor of claim 1 further comprising a second extending conducting element in electrical connection with the conductive interior, the second extending conducting element being in electrically conductive connection with the first electrode.

6. The electrochemical sensor of claim 5 wherein the first extending conducting element is spaced from the second extending conducting element within the conductive interior so that an electrically conductive pathway between the first extending conducting element and the second extending conducting element passes through the conductive interior of the first extending member.

7. The electrochemical sensor of claim 1 wherein the first electrode is formed from a conductive loaded polymeric material such that an interior thereof comprises conductive elements within a matrix of the polymeric material so that the interior is electrically conductive and an exterior surface thereof comprises the polymeric material and is less conductive than the interior, the conductive interior of the first electrode being placed in electrical connection with the first extending conducting element via the conducting interior of the first extending member.

8. The electrochemical sensor of claim 7 wherein at least a portion of the exterior surface of a first position of the first extending member is removed to expose the conductive interior of the first extending member at the first position thereof to form electrically conductive connection with a first portion of the first electrode from which the exterior surface of the first electrode has been removed to expose the conductive interior of the first electrode.

9. The electrochemical sensor of claim 8 wherein the first extending conducting element is spaced from the first position so that an electrically conductive pathway between the first extending conducting element and the first position passes through the conductive interior of the first extending member.

10. The electrochemical sensor of claim 7 further comprising a second extending conducting element in electrical connection with the conductive interior of the first extending member, the second extending conducting element being in electrically conductive connection with the first electrode.

11. The electrochemical sensor of claim 10 wherein the first extending conducting element is spaced from the second extending conducting element within the conductive interior of the first extending member so that an electrically conductive pathway between the first extending conducting element and the second extending conducting element passes through the conductive interior of the first extending member.

12. The electrochemical sensor of claim 7 further comprising an electrocatalytic material in electrically conductive contact with the conductive interior of the first electrode.

13. The electrochemical sensor of claim 12 wherein the polymeric material of the first connector, the polymeric material of the first electrode and a polymeric material of the housing are the same polymeric material.

14. The electrochemical sensor of claim 12 wherein the first extending conductive element comprises a metal.

15. The electrochemical sensor of claim 1 wherein the first extending conductive element comprises a metal.

16. The electrochemical sensor of claim 1 further comprising at least a second electrode and a second connector in electrically conductive connection with the second electrode, the second connector comprising a second extending member formed from a conductive loaded polymeric material, the second extending member being formed such that an interior thereof comprises conductive elements within a matrix of the polymeric material so that the interior is electrically conductive and an exterior surface thereof comprises the polymeric material and is less conductive than the conductive interior of the second extending member, the conductive interior of the second extending member being in electrically conductive connection with the second electrode, the second connector further comprising a first extending conductive element in electrical connection with the conductive interior of the second extending member, the first extending conductive element of the second connector extending from the second extending member to pass through the polymeric housing, a sealing bond being formed between the polymeric material of the second extending member and the polymeric housing.

17. The electrochemical sensor of claim 16 further comprising at least a third electrode and a third connector in electrically conductive connection with the third electrode, the third connector comprising a third extending member formed from a conductive loaded polymeric material, the third extending member being formed such that an interior thereof comprises conductive elements within a matrix of the polymeric material so that the interior is electrically conductive and an exterior surface thereof comprises the polymeric material and is less conductive than the conductive interior of the third extending member, the conductive interior of the third extending member being in electrically conductive connection with the third electrode, the third connector further comprising a first extending conductive element in electrical connection with the conductive interior of the third extending member, the first extending conductive element of the third connector extending from the third extending member to pass through the polymeric housing, a sealing bond being formed between the polymeric material of the third extending member and the polymeric housing.

18. The electrochemical sensor of claim 17 wherein the first electrode is a working electrode, the second electrode is a counter electrode and the third electrode is a reference electrode.

* * * * *